(12) United States Patent
Tsai

(10) Patent No.: US 11,712,793 B2
(45) Date of Patent: Aug. 1, 2023

(54) HOT STAPLER

(71) Applicant: GOODHOUSE Enterprise Co. Ltd., Taichung (TW)

(72) Inventor: Jung-Fa Tsai, Taichung (TW)

(73) Assignee: GOODHOUSE Enterprise Co. Ltd., Taichung (TW)

( * ) Notice: Subject to any disclaimer, the term of this patent is extended or adjusted under 35 U.S.C. 154(b) by 1070 days.

(21) Appl. No.: 16/454,124

(22) Filed: Jun. 27, 2019

(65) Prior Publication Data

US 2020/0406440 A1 Dec. 31, 2020

(51) Int. Cl.
| | |
|---|---|
| *B25C 5/15* | (2006.01) |
| *H05B 1/02* | (2006.01) |
| *H05B 3/06* | (2006.01) |
| *H05B 3/03* | (2006.01) |
| *B23K 3/03* | (2006.01) |
| *A61B 18/08* | (2006.01) |
| *B29C 73/04* | (2006.01) |
| *A61B 17/072* | (2006.01) |
| *A61B 18/10* | (2006.01) |

(52) U.S. Cl.
CPC ............... *B25C 5/15* (2013.01); *A61B 18/08* (2013.01); *B23K 3/0323* (2013.01); *H05B 1/0288* (2013.01); *H05B 3/03* (2013.01); *H05B 3/06* (2013.01); *A61B 17/072* (2013.01); *A61B 18/10* (2013.01); *B23K 3/0361* (2013.01); *B29C 73/04* (2013.01)

(58) Field of Classification Search
CPC . A61B 17/064; A61B 17/068; A61B 17/0644; A61B 17/072; A61B 18/08; A61B 18/082; A61B 18/10; B23K 3/0315; B23K 3/0323; B23K 3/0353; B23K 3/0361; H05B 1/0288; H05B 3/03; H05B 3/06; H05B 3/46; B25C 5/15
USPC ............... 227/19, 131, 156, 902; 606/1, 30; 219/209, 220, 227, 229, 225, 233, 238, 219/240, 236, 530, 533, 540
See application file for complete search history.

(56) References Cited

U.S. PATENT DOCUMENTS

| | | | | |
|---|---|---|---|---|
| 3,141,087 | A * | 7/1964 | Schoenwald | B23K 3/0323 219/229 |
| 3,408,478 | A * | 10/1968 | Joseph | B29C 66/1122 156/499 |
| 3,461,874 | A * | 8/1969 | Miguel | A61B 18/10 606/1 |
| 4,082,940 | A * | 4/1978 | Knowles | B23K 3/0361 219/541 |

(Continued)

*Primary Examiner* — Scott A Smith
(74) *Attorney, Agent, or Firm* — Alan D. Kamrath; Karin L. Williams; Mayer & Williams PC

(57) ABSTRACT

A hot stapler includes a body, two heat conducting units, an electrical storage unit, a circuit unit, and a switch button. The body includes a head and a handle. The electrical storage unit is disposed in the handle and has a voltage value less than 6 volts. A first wire and a first resistor of the circuit unit are electrically mounted between one of the two heat conducting units and the electrical storage unit. A second wire and a second resistor of the circuit unit are electrically mounted between the other one of the two heat conducting units and the electrical storage unit. The switch button is disposed on the handle and is switchable between a power-on position and a power-off position.

6 Claims, 5 Drawing Sheets

(56) References Cited

U.S. PATENT DOCUMENTS

| | | | | |
|---|---|---|---|---|
| 4,303,825 | A * | 12/1981 | Jaronen | E05B 17/0016 |
| | | | | 219/202 |
| 4,359,052 | A * | 11/1982 | Staub | A61B 18/10 |
| | | | | 219/233 |
| 4,563,570 | A * | 1/1986 | Johns | A61B 18/082 |
| | | | | 219/233 |
| 4,606,342 | A * | 8/1986 | Zamba | A61B 18/082 |
| | | | | 606/30 |
| 5,446,262 | A * | 8/1995 | McCambridge | B23K 3/0315 |
| | | | | 219/229 |
| 9,339,884 | B2 * | 5/2016 | Tsai | B23K 3/0323 |
| 9,403,229 | B2 * | 8/2016 | Tsai | B23K 3/0361 |
| 10,189,104 | B2 * | 1/2019 | Tsai | B23K 3/0361 |
| 2005/0015080 | A1 * | 1/2005 | Ciccone | A61B 18/08 |
| | | | | 219/233 |
| 2014/0091075 | A1 * | 4/2014 | Liu | B29C 66/43 |
| | | | | 219/209 |
| 2015/0196966 | A1 * | 7/2015 | Tsai | B23K 3/0323 |
| | | | | 219/238 |
| 2015/0224590 | A1 * | 8/2015 | Tsai | B23K 3/0323 |
| | | | | 219/240 |
| 2016/0100456 | A1 * | 4/2016 | Tsai | H05B 3/46 |
| | | | | 219/533 |
| 2016/0332246 | A1 * | 11/2016 | Tsai | B23K 3/0323 |

* cited by examiner

HOT STAPLER

BACKGROUND

The present invention relates to a heating implement and, more particular, to a hot stapler for plastic repair.

In general, broken fittings on headlight assemblies, torn tabs, bumpers, or any other plastic component are difficult to repair via adhesion. Therefore, welding is most commonly used for plastic repair. The present hot staple tool for plastic repair operates on 110 V or 220 V AC so that it must be applied in a place where a power supply is provided, and is not suitable for various narrow working environments due to interference from the power line.

Thus, a need exists for a novel hot stapler to mitigate and/or obviate the above disadvantages.

SUMMARY

A hot stapler according to the present invention comprises a body, a two heat conducting units, an electrical storage unit, a circuit unit, and a switch button. The body includes a head and a handle. The two heat conducting units are adapted to connect with two legs of a staple. One end of each heat conducting unit is inserted into the head, and the other end of each heat conducting unit is exposed out of the body. The electrical storage unit is disposed in the handle and has a voltage value less than 6 volts. The circuit unit includes a first wire, a first resistor electrically connected to the first wire, a second wire, and a second resistor electrically connected to the second wire. The first wire and the first resistor are electrically mounted between one of the two heat conducting units and the electrical storage unit. The second wire and the second resistor are electrically mounted between the other one of the two heat conducting units and the electrical storage unit. The switch button is disposed on the handle and is switchable between a power-on position and a power-off position, so that current supplied by the electrical storage unit can flow through the first wire, the first resistor, the second wire, and the second resistor to generate thermal energy to heat the staple.

In an example, the electrical storage unit includes two primary batteries connected in series.

In an example, each primary battery has a nominal voltage of 1.5 volts.

In an example, the electrical storage unit includes a secondary battery.

In an example, the secondary battery is a lithium-ion battery or a nickel-metal-hydride battery.

In an example, the secondary battery has a nominal voltage of 3.7 volts.

In an example, the resistance values of the first resistor and the second resistor both are in the range of from 0.06 ohms to 0.2 ohms.

In an example, each heat conducting unit includes a guiding pipe, an electrical insulation tube mounted around the guiding pipe, and a heat conducting pipe mounted around the electrical insulation tube. The heat conducting pipe has a radial hole and an axial hole disposed on an end face thereof to be adapted to connect with one of the two legs of the staple. The first wire and the second wire are respectively inserted into the two guiding pipes of the two heat conducting units and are respectively bent to hook with the two radial holes of the two heat conducting pipes.

In an example, the switch button is slidably mounted on the handle.

In an example, the first wire is electrically connected to a negative electrode of the electrical storage unit, and the second wire is electrically connected to a positive electrode of the electrical storage unit.

The present invention will become clearer in light of the following detailed description of illustrative embodiments of this invention described in connection with the drawings.

BRIEF DESCRIPTION OF THE DRAWINGS

The aforementioned and other aspects of the invention may best be understood by reference to the following description taken in conjunction with the accompanying drawings in which.

DETAILED DESCRIPTION

Figure 1:
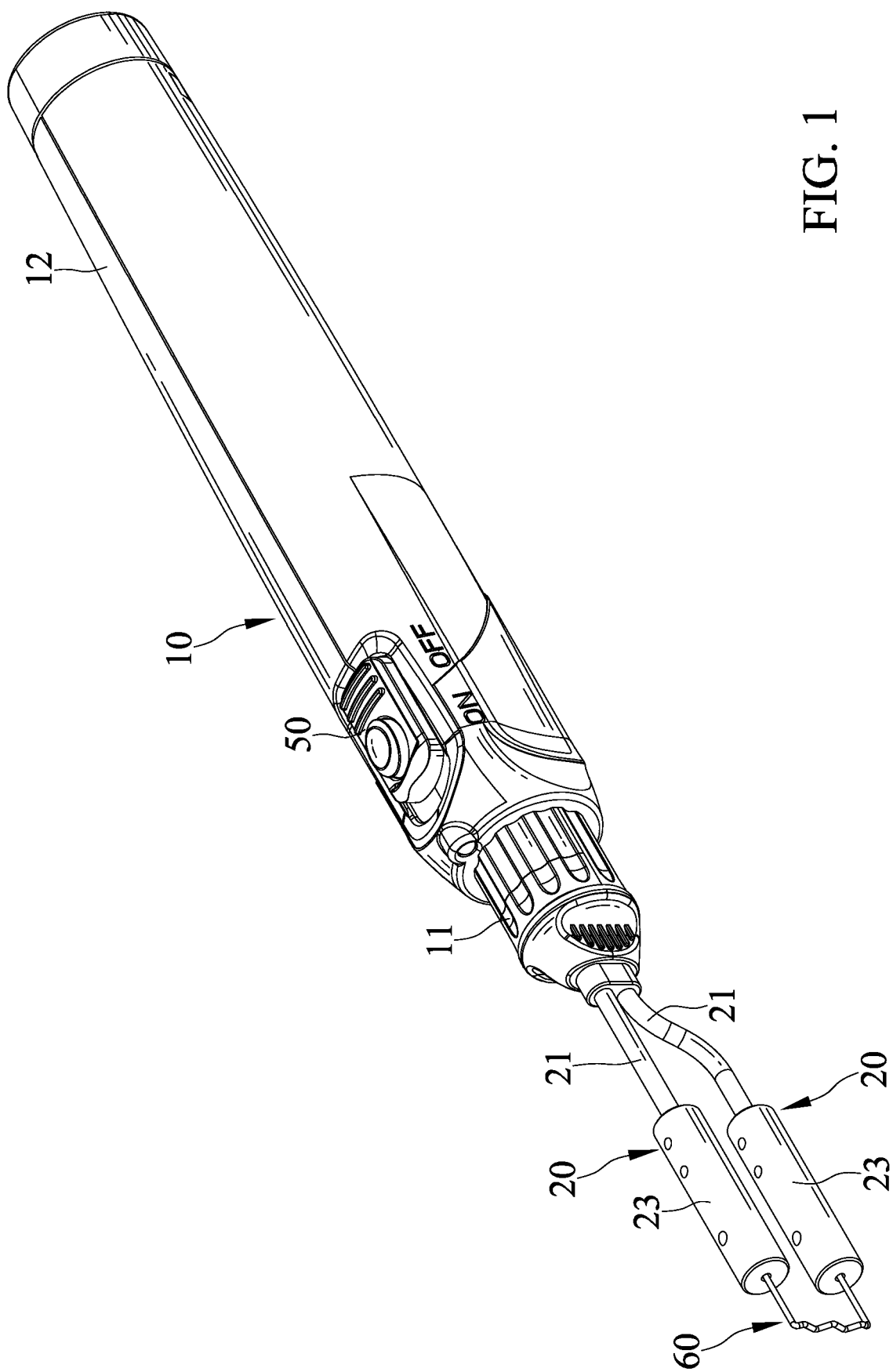
FIG. 1 is a perspective view of a hot stapler according to the present invention.
Figure 2:
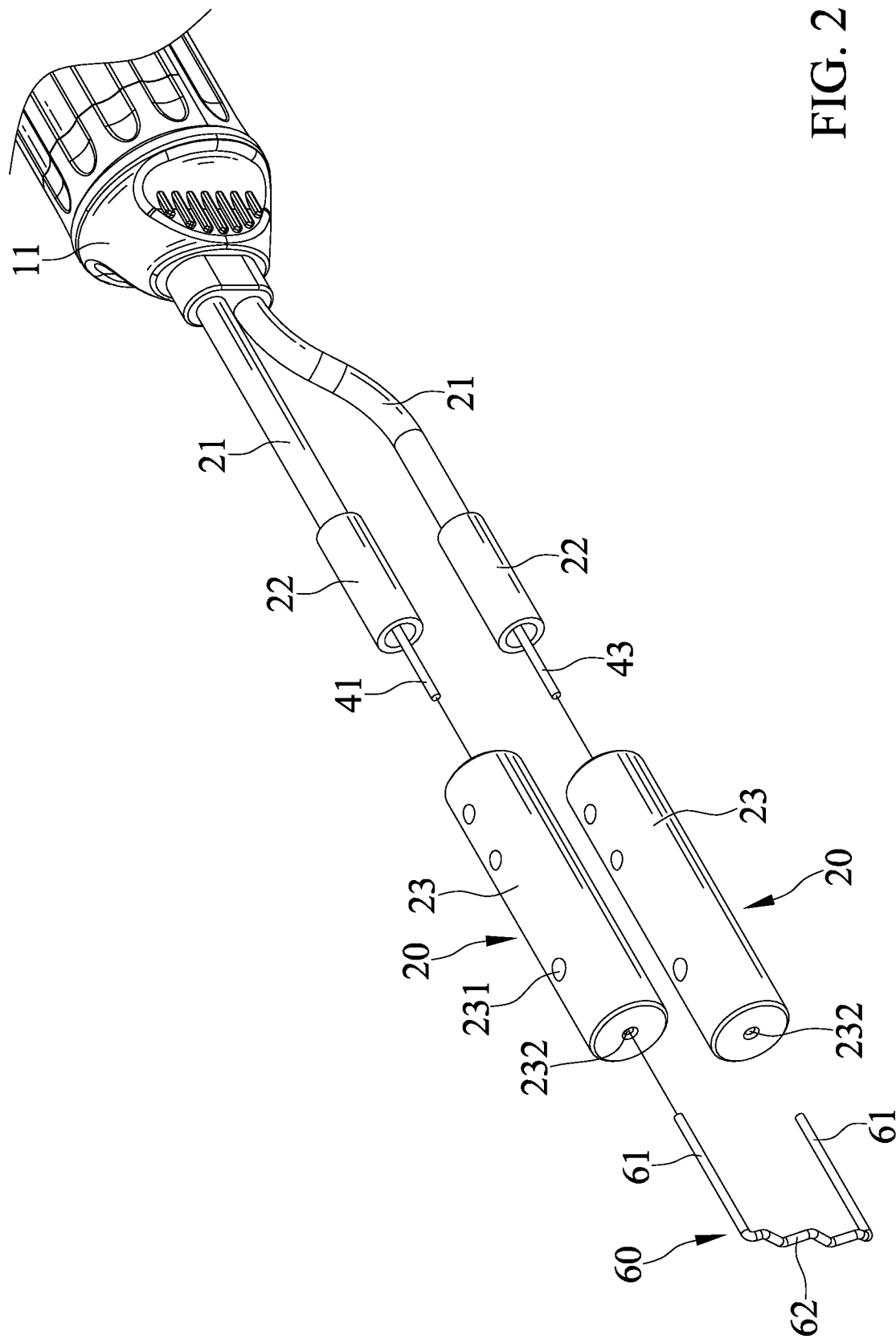
FIG. 2 is a partial exploded perspective view of the hot stapler of FIG. 1.
Figure 3:
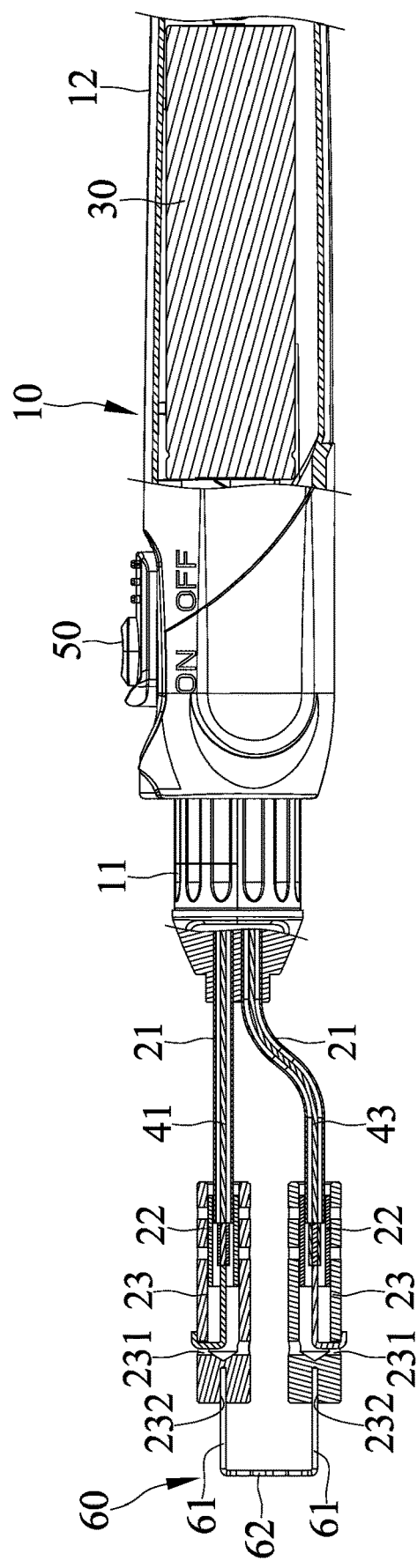
FIG. 3 is a partial cross-sectional view of the hot stapler of FIG. 1.
Figure 4:
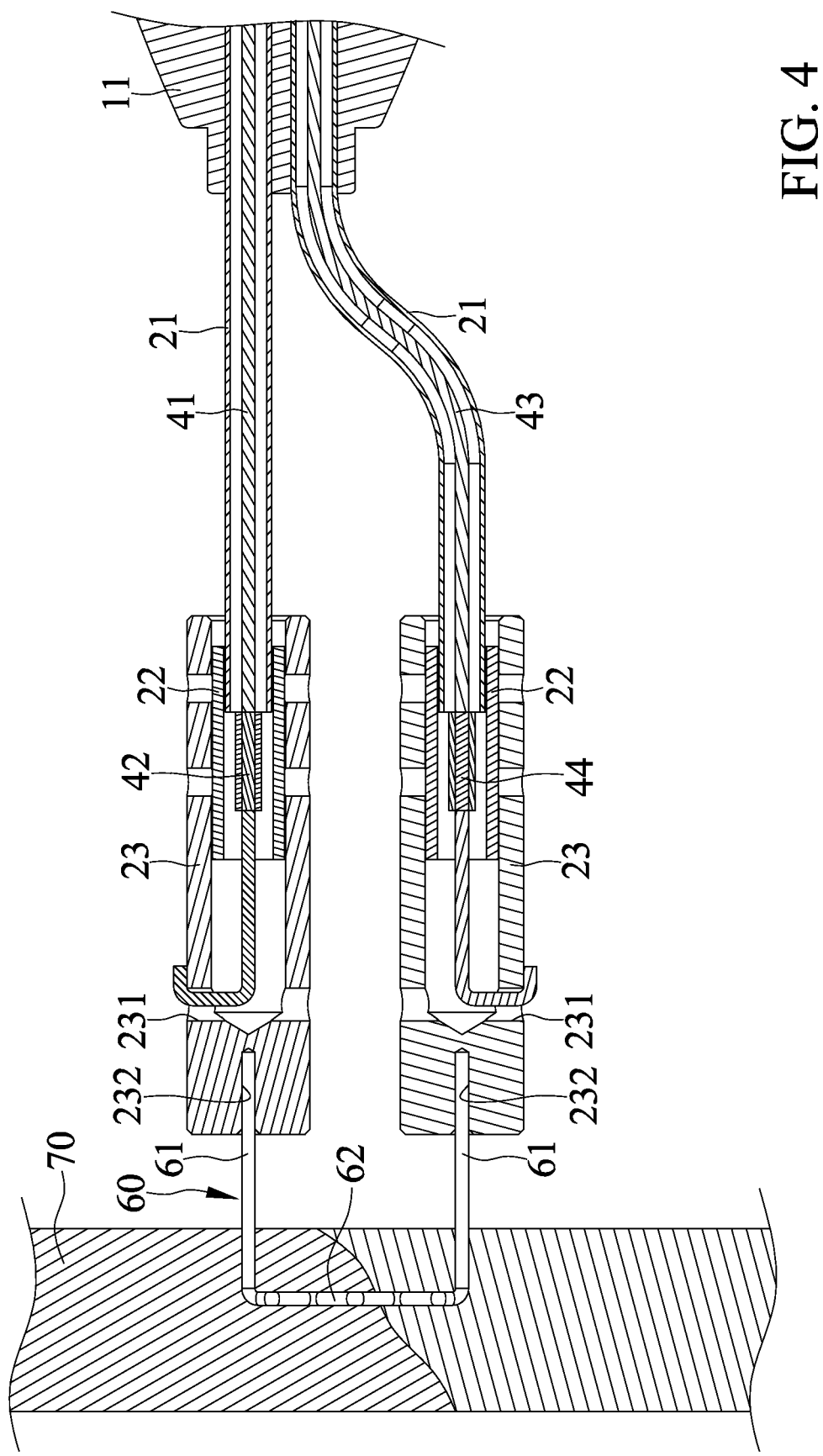
FIG. 4 is another partial cross-sectional view of the hot stapler of FIG. 1 and shows the hot stapler using heat to embed a staple into the plastic to stitch tears in plastic back together.
Figure 5:
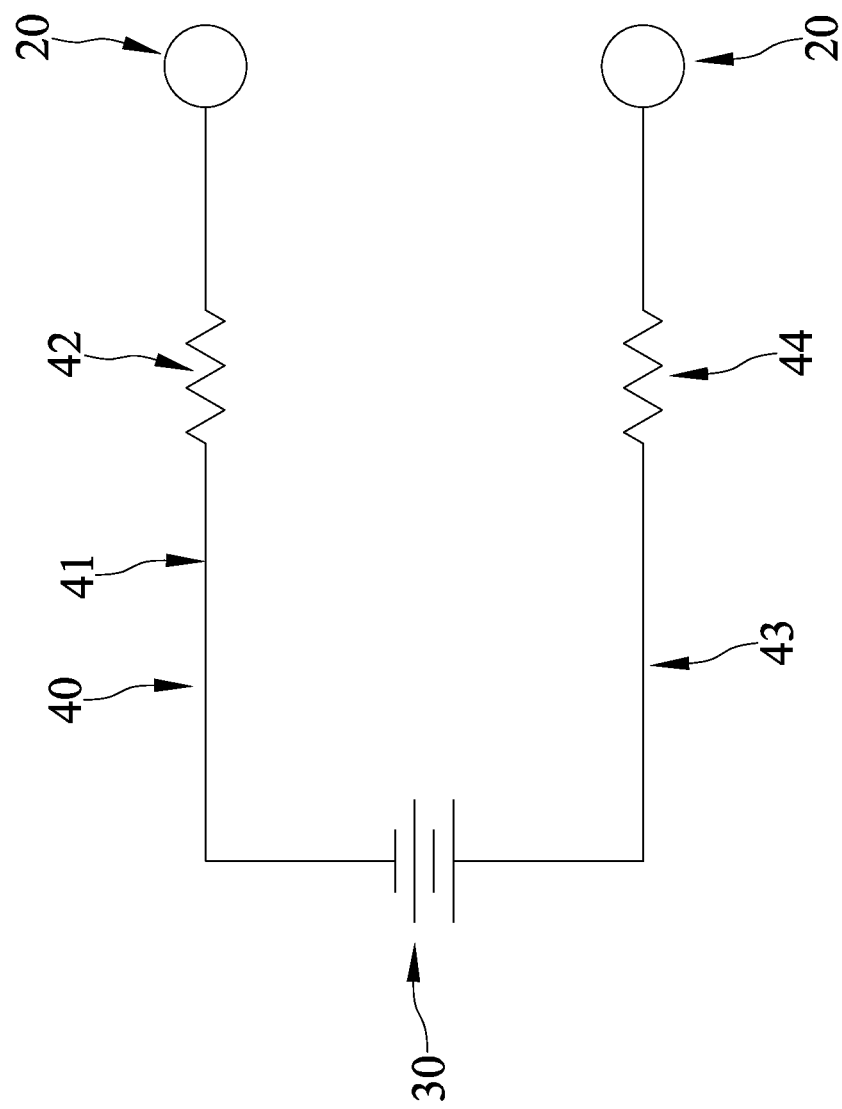
FIG. 5 is a circuit diagram of the hot stapler of FIG. 1.

FIGS. 1-5 show a hot stapler according to the present invention. The hot stapler includes a body 10, two heat conducting units 20, an electrical storage unit 30, a circuit unit 40, and a switch button 50.

The body 10 includes a head 11 and a handle 12. The two heat conducting units 20 are adapted to connect with two legs 61 of a staple 60 (shown in FIG. 4). One end of each heat conducting unit 20 is inserted into the head 11, and the other end of each heat conducting unit 20 is exposed out of the body 10. Each heat conducting unit 20 includes a guiding pipe 21, an electrical insulation tube 22 mounted around the guiding pipe 21, and a heat conducting pipe 23 mounted around the electrical insulation tube 22. The heat conducting pipe 23 of each heat conducting unit 20 has a radial hole 231 and an axial hole 232 disposed on an end face of the heat conducting pipe 23 to be adapted to connect with one of the two legs 61 of the staple 60. Preferably, the heat conducting pipe 23 of each heat conducting unit 20 may be made of metal to enhance heat conduction and dissipation effect.

The electrical storage unit 30 is disposed in the handle 12 and has a voltage value less than 6 volts. The electrical storage unit 30 may include two or more than two primary batteries connected in series, and each primary battery has a nominal voltage of 1.5 volts. Further, the electrical storage unit 30 may include at least one secondary battery, the secondary battery may be a lithium-ion battery or a nickel-metal-hydride battery, and the secondary battery has a nominal voltage of 3.7 volts.

The circuit unit 40 includes a first wire 41, a first resistor 42 electrically connected to the first wire 41, a second wire 43, and a second resistor 44 electrically connected to the second wire 43. The first wire 41 and the first resistor 42 are electrically mounted between one of the two heat conducting units 20 and the electrical storage unit 30, and the second wire 43 and the second resistor 44 are electrically mounted between the other one of the two heat conducting units 20 and the electrical storage unit 30. The first wire 41 is electrically connected to a negative electrode of the electrical storage unit 30, and the second wire 43 is electrically connected to a positive electrode of the electrical storage unit 30. The first wire 41 and the second wire 43 are respectively inserted into the two guiding pipes 21 of the two heat conducting units 20 and are respectively bent to hook with the two radial holes 231 of the two heat conducting pipes 23, so that the first wire 41 and the second wire 43 can be fixedly connected to the two heat conducting pipes 23. Further, the resistance values of the first resistor 42 and the second resistor 44 both are in the range of from 0.06 ohms to 0.2 ohms. Furthermore, the first resistor 42 and the second resistor 44 have the same resistance value.

The switch button 50 is slidably mounted on the handle 12 and is switchable between a power-on position and a power-off position, so that current supplied by the electrical storage unit 30 can flow through the first wire 41, the first resistor 42, the second wire 43, and the second resistor 44 to generate thermal energy to heat the staple 60.

The two legs 61 of the staple 60 are inserted into the two axial holes 232 of the two heat conducting pipes 23 and are heated when the switch button 50 is switched to the power-on position, so that the staple 60 is heated to high temperature to cause a central part 62 of the staple 60 being able to embed into the plastic 70 to stitch tears in plastic 70 back together. Therefore, the hot stapler is configured to prevent the interference from the conventional power line via the electrical storage unit 30, and can quickly heat the staple 60 by low voltage power supply via the first resistor 42 and the second resistor 44.

While various embodiments have been described above, it should be understood that they have been presented by way of example only, and not limitation. For example, any of the elements associated with the privacy summary may employ any of the desired functionality set forth hereinabove. Thus, the breadth and scope of a preferred embodiment should not be limited by any of the above-described exemplary embodiments.

What is claimed is:

1. A hot stapler comprising:
    a bod including a head and a handle;
    two heat conducting units adapted to connect with two legs of a staple, with one end of each heat conducting unit inserted into the head, and with the other end of each heat conducting unit exposed out of the body, wherein each heat conducting unit includes a guiding pipe, an electrical insulation tube mounted around the guiding pipe, and a heat conducting pipe mounted around the electrical insulation tube, wherein the heat conducting pipe has a radial hole and an axial hole disposed on an end face thereof to be adapted to connect with one of the two legs of the staple;
    an electrical storage unit disposed in the handle and having a voltage value less than 6 volts;
    a circuit unit including a first wire, a first resistor electrically connected to the first wire, a second wire, and a second resistor electrically connected to the second wire, with the first wire and the first resistor electrically mounted between one of the two heat conducting units and the electrical storage unit, and with the second wire and the second resistor electrically mounted between the other one of the two heat conducting units and the electrical storage unit, and wherein the first wire and the second wire are respectively inserted into the two guiding pipes of the two heat conducting units and are respectively bent to hook with the two radial holes of the two heat conducting pipes; and
    a switch button disposed on the handle and being switchable between a power-on position and a power-off position, so that current supplied by the electrical storage unit can flow through the first wire, the first resistor, the second wire, and the second resistor to generate thermal energy to heat the staple.

2. The hot stapler as claimed in claim 1, wherein the electrical storage unit includes two primary batteries connected in series.

3. The hot stapler as claimed in claim 2, wherein each primary battery has a nominal voltage of 1.5 volts.

4. The hot stapler as claimed in claim 1, wherein the resistance values of the first resistor and the second resistor both are in the range of from 0.06 ohms to 0.2 ohms.

5. The hot stapler as claimed in claim 1, wherein the switch button is slidably mounted on the handle.

6. The hot stapler as claimed in claim 1, wherein the first wire is electrically connected to a negative electrode of the electrical storage unit, and wherein the second wire is electrically connected to a positive electrode of the electrical storage unit.

* * * * *